US00RE48734E

(19) United States
(12) Reissued Patent
Masleid et al.

(10) Patent Number: US RE48,734 E
(45) Date of Reissued Patent: Sep. 14, 2021

(54) METHOD AND APPARATUS FOR DETERMINING THE HEALTH AND REMAINING SERVICE LIFE OF AUSTENITIC STEEL REFORMER TUBES AND THE LIKE

(71) Applicant: ARCELORMITTAL, Luxembourg (LU)

(72) Inventors: Michael A. Masleid, Dyer, IN (US); Zofia E. Niemczura, Porter, IN (US); George B. Tsvik, Valparaiso, IN (US)

(73) Assignee: ArcelorMittal, Luxembourg (LU)

(21) Appl. No.: 15/936,649

(22) Filed: Mar. 27, 2018

Related U.S. Patent Documents

Reissue of:
(64) Patent No.: 9,546,982
Issued: Jan. 17, 2017
Appl. No.: 14/102,378
Filed: Dec. 10, 2013

U.S. Applications:
(60) Provisional application No. 61/735,505, filed on Dec. 10, 2012.

(51) Int. Cl.
*G01N 27/90* (2021.01)
*G01N 27/82* (2006.01)
*G01N 27/83* (2006.01)

(52) U.S. Cl.
CPC ..... *G01N 27/9046* (2013.01); *G01N 27/82* (2013.01); *G01N 27/83* (2013.01)

(58) Field of Classification Search
CPC ..... G01N 27/82; G01N 27/83; G01N 27/9046
See application file for complete search history.

(56) References Cited

U.S. PATENT DOCUMENTS 4,084,136 A * 4/1978 Libby ..... G01R 31/2831 324/238
5,047,717 A * 9/1991 Hofer ..... G01N 27/72 324/209
5,180,969 A * 1/1993 Kwun ..... G01N 27/904 324/240
5,311,127 A * 5/1994 Bisiaux ..... G01N 27/9046 324/232

(Continued)

FOREIGN PATENT DOCUMENTS

GB 2088064 A 6/1982
JP S61201159 A 9/1986

(Continued)

OTHER PUBLICATIONS

Kenneth Short, "Microprocessors and Programmed Logic", second edition, ISBN 0-13-580606-2 (Year: 1987).*

*Primary Examiner* — Minh Nguyen
(74) *Attorney, Agent, or Firm* — Davidson, Davidson & Kappel, LLC

(57) ABSTRACT

Testing methods and apparatus for testing the health of steel tubes used in reformers and other tubes and pipes used in other high temperature applications. The method includes the steps of transmitting two sinusoidal electromagnetic signals, each having a different frequency F1 and F2, into the reformer tube, receiving a response signal, and analyzing the received response signal's intermodulation frequencies to determine the state of the steel reformer tube.

16 Claims, 7 Drawing Sheets

(56) References Cited

U.S. PATENT DOCUMENTS

| | | | | |
|---|---|---|---|---|
| 5,616,850 | A | 4/1997 | Sage | |
| 6,201,391 | B1 * | 3/2001 | Burkhardt | G01N 27/82 324/233 |
| 6,211,671 | B1 * | 4/2001 | Shattil | H05K 9/00 324/225 |
| 6,239,593 | B1 | 5/2001 | Burkhardt | |
| 6,275,050 | B1 * | 8/2001 | Born | G01N 17/00 204/404 |
| 6,344,739 | B1 * | 2/2002 | Hardy | G01N 27/902 324/220 |
| 6,597,993 | B2 | 7/2003 | Strickland et al. | |
| 6,917,176 | B2 | 7/2005 | Schempf | |
| 6,995,558 | B2 | 2/2006 | Butters et al. | |
| 7,002,340 | B2 * | 2/2006 | Atherton | G01N 33/383 324/220 |
| 7,046,356 | B2 | 5/2006 | Bondurant | |
| 7,449,881 | B2 | 11/2008 | Edwin et al. | |
| 8,050,874 | B2 | 11/2011 | Papadimitriou et al. | |
| 8,193,804 | B2 | 6/2012 | Hong et al. | |
| 8,274,279 | B2 * | 9/2012 | Gies | G01N 27/9033 324/200 |
| 8,378,676 | B2 | 2/2013 | Ceschini et al. | |
| 8,536,860 | B2 * | 9/2013 | Boenisch | G01N 27/90 324/220 |
| 8,928,315 | B2 | 1/2015 | Hashimoto et al. | |
| 10,060,882 | B2 | 8/2018 | Masleid et al. | |
| 2001/0019264 | A1 * | 9/2001 | Shattil | H05K 9/00 324/225 |
| 2003/0100994 | A1 * | 5/2003 | Strickland | G01V 3/28 702/7 |
| 2004/0114793 | A1 | 6/2004 | Bondurant et al. | |
| 2004/0183530 | A1 * | 9/2004 | Butters | G01R 33/032 324/248 |
| 2006/0050092 | A1 * | 3/2006 | Bondurant | G06T 7/0004 345/664 |
| 2006/0119492 | A1 | 6/2006 | Kim | |
| 2008/0004839 | A1 * | 1/2008 | Papadimitriou | G01N 27/9046 702/182 |
| 2011/0163740 | A1 * | 7/2011 | Russell | G01N 27/72 324/220 |
| 2012/0007596 | A1 * | 1/2012 | Hashimoto | G01N 27/902 324/240 |
| 2012/0089346 | A1 * | 4/2012 | Huyse | G06Q 10/06 702/34 |
| 2012/0152007 | A1 | 6/2012 | Holmes | |
| 2013/0060487 | A1 * | 3/2013 | Papadimitriou | G10L 15/22 702/34 |
| 2015/0177191 | A1 * | 6/2015 | Hardy | G01N 27/904 324/222 |
| 2016/0195496 | A1 | 7/2016 | Masleid | |

FOREIGN PATENT DOCUMENTS

| | | | |
|---|---|---|---|
| JP | H0526811 | A | 2/1993 |
| JP | 2003149212 | A | 5/2003 |
| JP | 2004279054 | A | 10/2004 |
| JP | 2004279055 | A | 10/2004 |
| JP | 2007206057 | A | 8/2007 |
| JP | 2010204101 | A | 9/2010 |
| KR | 10-2005-0026504 | A | 3/2005 |
| KR | 1020120031939 | A | 4/2012 |
| RU | 2397485 | C2 | 8/2010 |
| RU | 115073 | U1 | 4/2012 |
| RU | 2010141693 | A | 4/2012 |
| RU | 2494249 | C2 | 9/2013 |

* cited by examiner

METHOD AND APPARATUS FOR DETERMINING THE HEALTH AND REMAINING SERVICE LIFE OF AUSTENITIC STEEL REFORMER TUBES AND THE LIKE

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

*Notice: More than one reissue application has been filed for the reissue of U.S. Pat. No. 9,546,982. The reissue applications are application Ser. Nos. 15/936,649, which is the present application, and 17/238,487, which is a reissue continuation of the present application.*

CROSS-REFERENCE TO RELATED APPLICATIONS

This [Application] *application is an application for reissue of application Ser. No. 14/102,378 filed on Dec. 10, 2013 which issued on Jan. 17, 2017 as U.S. Pat. No. 9,546,982, which* claims the benefit under 35 U.S.C. 119(e) of U.S. Provisional Application No. 61/735,505 filed Dec. 10, 2012.

FIELD OF THE INVENTION

The present invention relates generally to non-destructive testing methods and apparatuses therefor. More specifically it relates to a non-destructive testing (NDT) method and apparatus for austenitic steel reformer tubes and the like. Most specifically it relates to an electromagnetic method and apparatus for the early detection of deleterious changes in the alloy's microstructure before any other available NDT methods can detect them, thereby estimating the health and remaining service life for in-service austenitic steel reformer tubes.

BACKGROUND OF THE INVENTION

Austenitic steel reformer tubes are used in many chemical processes. Examples include tubes used to produce ammonia, methanol, hydrogen, nitric and sulfuric acids, and cracking of petroleum. Reformer tubes, also called catalyst tubes, are one of the highest cost components of such plants both in capital and maintenance. A typical installation consists of several hundred vertical tubes. These tubes represent a significant cost for replacement and can be a major source of plant unavailability if unplanned failures occur.

Such tubes are typically subjected to high temperatures, temperature gradients, pressure changes and contact with corrosive substances. Under such situations creep, metal dusting, and surface irregularities frequently develop. Creep is a diffusion related process that develops gradually. The signs are not noticeable by reformer operator. Creep forms microscopic voids which coalescence and eventually form creep fissure (cracks). If left untreated, creep will develop into cracks that will propagate leading to catastrophic failure of the tube during service.

The plant operator is faced with balancing production needs against tube life and risk of tube failure. During plant operation the catalyst filled tubes are externally heated to allow the reforming reaction to occur. One of the major concerns in plant operation is that the reformer tubes operate at a highly elevated temperature (up to 1150-1200° C.) such that they are susceptible to the failure mechanism referred to above as "creep". This condition exists due to the elevated temperatures and stresses imposed by internal pressure, thermal gradients, and mechanical loading cycles. Being able to identify and locate such damage in its early stages is essential for optimizing plant operation and extending the tube's useful service life.

Known Non-Destructive Testing (NDT) methods based on intermodulation measurements are used to find nonlinear conductive materials contained in a non conductive substrate. A different method is needed to deal with non-linear magnetic materials contained in a conductive substrate. Existing NDT methods for austenitic steel are based on laser shape measurement, eddy current testing for surface cracks, and ultrasound testing for subsurface cracks. These methods are useful, but tell little or nothing about changes early in the life of the material. In addition, the existing methods require knowledge of the initial conditions of the material and are subject to error due to changes in surface conditions.

Conventional NDT inspection techniques currently applied to reformer tubes are geared to finding creep damage in the form of internal cracking. However, with the trend towards larger tube diameters and longer intervals between turnarounds, the detection of such defects may not allow for sufficient time for forward planning of tube replacements. Also, such "end of life" techniques do not allow any differentiation between the "good" tubes and the "bad" tubes. Early detection of underutilized tube life can prevent the lost opportunity on both unrealized production through running them too cool and tube life "giveaway" if good tubes are discarded prematurely.

Typically, destructive testing is used on a small number of tubes removed from the reformer to try and determine the absolute life remaining. Whatever method is used, the results are used on a sample size that is not statistically valid. It is preferable that all the tubes be surveyed with a NDT technique to characterize their relative condition.

Reformer tubes undergo creep strain, in the form of longitudinal and/or diametrical growth, from the first day that they are fired. Measuring the creep elongation of such tubes is the most popular deterioration detection method in routine use today, but this method is very inaccurate for monitoring in service tube deterioration. This because there is no known method for measuring the local longitudinal growth, just total growth which is averaged over the whole length of the tube.

Measuring the diametrical growth is more accurate but could can lead to inaccurate measurements early in the service life of a tube due to the scale effect. That is, accurate measurement of circumferential growth is complicated by the growth and sloughing of a corrosion layer (scale) on the surface of the tube which mimics diametrical expansion. Measuring the diametrical growth also requires tube climbing equipment.

The ability to accurately measure and record tube deterioration means that the tubes' condition can be monitored on day one. Therefore, not only can individual tubes be retired from service at an appropriate time, but also the reformer as a whole can be assessed for performance.

To get an idea of the scope of the problem to be solved, one should note that, at present, ArcelorMittal has 8 reformers that use about 2.500 reformer tubes. Tubes are quite expensive, costing more than $30,000 each, plus catalyst costs which doubles the tube cost along with cost of installation. Reformers operate continuously from 2 to 5 years between cold shutdowns.

A method is needed to evaluate the tube current condition during scheduled cold shutdown and remove the bad tubes to prevent the catastrophic failure of any tubes during the 2-5 year operation period. Such a failure could result in premature shutdown of the reformer and significant loss of time and money.

In addition, a tool is needed to assess performance of the reformer as a whole because reformer operation conditions may not be consistent from one reformer region to another. If increase in the tubes' deterioration is faster in certain reformer regions, it indicates that reformer operation condition is not well balanced. The fine-tuning of the reformer for better balance will improve productivity and save tubes that otherwise would deteriorate faster in this area. The object is to detect reformer operation abnormality early enough to prevent the tubes' faster deterioration since the changes occurring in the tube microstructure due to operation condition are irreversible.

Accordingly, there is a need for an automated method and apparatus for the examination of reformer tubes. The method should be nondestructive and able to detect very early changes in tube alloy to allow for reformer adjustment when there is still time to save the tubes. Furthermore the method and apparatus should be able to provide an estimated "reminder of tube life" to assist in tube replacement decisions.

SUMMARY OF THE INVENTION

The present invention comprises a method and apparatus for measuring/testing the degree of deterioration of an austenitic steel reformer tube. The present method capitalizes on the metallurgical phenomenon that, as the paramagnetic tube alloy deteriorates, it develops ferromagnetic regions that, in early stages, are extremely small and undetectable by any other available method. The present inventors have found good correlation between the alloy magnetic properties, and the lifetime of the heat-resistant Cr—Ni alloy tubes. The present method and apparatus design utilizes the correlation found between the alloy's magnetic properties, structural transformation and the service lifetime of the heat-resistant Cr—Ni alloy tubes. The method and apparatus utilizes the correlation to measure thermal damage of the tubes caused by the high-temperature service environment.

The method includes the steps of providing a sample austenitic steel reformer tube to be tested, choosing one or more testing positions on said an austenitic steel reformer tube, transmitting two sinusoidal electromagnetic signals, each having a different frequency $F_1$ and $F_2$, into a test position on the austenitic steel reformer tube, receiving a response signal from said test position, and analyzing said received response signal's fundamental and intermodulation frequency magnitudes to determine the state of the austenitic steel reformer tube at said test position.

The step of receiving a response signal from the test position may include receiving an analog response signal on a receiver coil. The step of receiving a response signal from the test position may further include the step of converting the analog response signal to a digital response signal, using an analog to digital converter. The analog to digital converter may have a sampling frequency $F_s$. The step of converting the analog response signal to a digital response signal, using an analog to digital converter may include combining a multiple of samples into a single representative sample, the number of samples which are combined into said single representative sample may be designated as the sample size $S_s$. The sample size $S_s$ may be an integral power of 2. The sample size $S_s$ may be a number selected from the group consisting of 4096, 8192, and 16384 samples. The sampling frequency $F_s$ may be 44100 samples per second.

The step of transmitting two sinusoidal electromagnetic signals may include the step of defining a base frequency $F_0$, wherein $F_0=F_s/S_s$. The step of transmitting two sinusoidal electromagnetic signals may further include the step of choosing the two frequencies F1 and F2 such that: $F_1=N\times F_0$; $F_2=P\times F_0$; where N and P are integers with N not equal to P, and N and P are chosen such that none of the intermodulation frequencies, $F(Q,R)=Q\times F_1+R\times F_2$ are equal to an integral multiple of $F_1$ or $F_2$ for small, non-zero, integer (positive or negative) values of Q and R.

The step of transmitting two sinusoidal electromagnetic signals may comprise transmitting both signals from a single transmitter coil, or may comprise transmitting each of the signals from individual transmitter coils. The transmitter coils may have a larger diameter than the thickness of the sample tube to be tested. The step of transmitting two sinusoidal electromagnetic signals may comprise creating analog sinusoidal electromagnetic signals using at least one digital-to-analog signal generator. The two sinusoidal electromagnetic signals may also be created by two signal generators.

The step of analyzing the received response signal's fundamental and intermodulation frequencies may comprise analyzing the first order fundamental and third order intermodulation frequencies of said received response signal. The Fundamental may be $F_2$. The third order intermodulation frequencies may be $2F_1+F_2$ and $F_1+2F_2$. The step of analyzing the third order intermodulation frequencies may comprise converting the ratio of the magnitude of the third order intermodulation frequencies to the magnitude of the fundamental frequency into decibels dB.

The strength of the third order intermodulation frequencies which have been converted into decibels dB may be compared to the same measurement of brand new and end of service life austenitic steel reformer tubes, the comparison may providing a qualitative measure of the health of the austenitic steel reformer tube. The method may include the further step of estimating the remaining service life of the austenitic steel reformer tube as a fraction of the present service life of the austenitic steel reformer tube by the following formulas:

$$\text{fractional life remaining } L_r=|S_e-S_n|/S_e-S_0|; \text{ and}$$

$$\text{estimated lifetime remaining } T_r=(L_r/(1-L_r))\times T_n$$

where:

$L_r$ is the estimated percentage of life remaining;

$S_e$ is the third order intermodulation frequencies signal strength converted into decibels dB of an austenitic steel reformer tube at the end of service life;

$S_n$ is the third order intermodulation frequencies signal strength converted into decibels dB of the test sample now;

$S_0$ is either the third order intermodulation frequencies signal strength when there is no tube present under the probe, or the third order intermodulation frequencies signal strength of a new tube that has been heated to operating temperature for a few hours, whichever is higher;

$T_r$ is the estimated service lifetime remaining for the test sample; and $T_n$ is the present service life of the test sample.

DETAILED DESCRIPTION OF THE INVENTION

The present invention relates to measurement/testing methods and apparatus for testing the health of steel tubes used in reformers and other tubes and pipes used in other high temperature applications. The inventors use an electromagnetic intermodulation technique to measure ferromagnetism generated in the paramagnetic alloy during service. The ferromagnetic signal is initially small, but increases with length of service and severity of the thermal environment. Conventional eddy current NDT methods are not able to detect this very low level of deterioration. It is believed that the ferromagnetism, in the initial stage of deterioration, develops in the sub-scale Cr-depleted zones of the tube wall, around the carbides and along the grain boundaries, thus creating the discrete network of ferromagnetic channels throughout the paramagnetic material.

In order to apply signal intermodulation techniques through a conductive media (i.e. the steel reformer tubes) it is necessary to use extra low frequency signals in order to penetrate quickly throughout the substrate. The field configuration must be chosen to ignore surface effects and to provide reasonably uniform sensitivity throughout the substrate. Signal processing techniques are used to achieve enough sensitivity. In addition, because deterioration and failure of these materials is a local phenomenon, it is necessary to be able to scan the entire substrate, preferably as quickly as possible.

Generically the method consists of using the probe of the present invention to transmit a pair of electromagnetic signals at different frequencies into the material to be tested. The probe then records the response of the material to the pair of signals, and this response is used to determine the physical state of the material.

To more fully understand the present inventions, the probe and the testing criterion/technique will be described. Thereafter, the specifics of use of the probe and technique to determine the health and projected useful life expectancy of steel tubes that have been subjected to high temperature environments will be described.

The Probe

Figure 1:
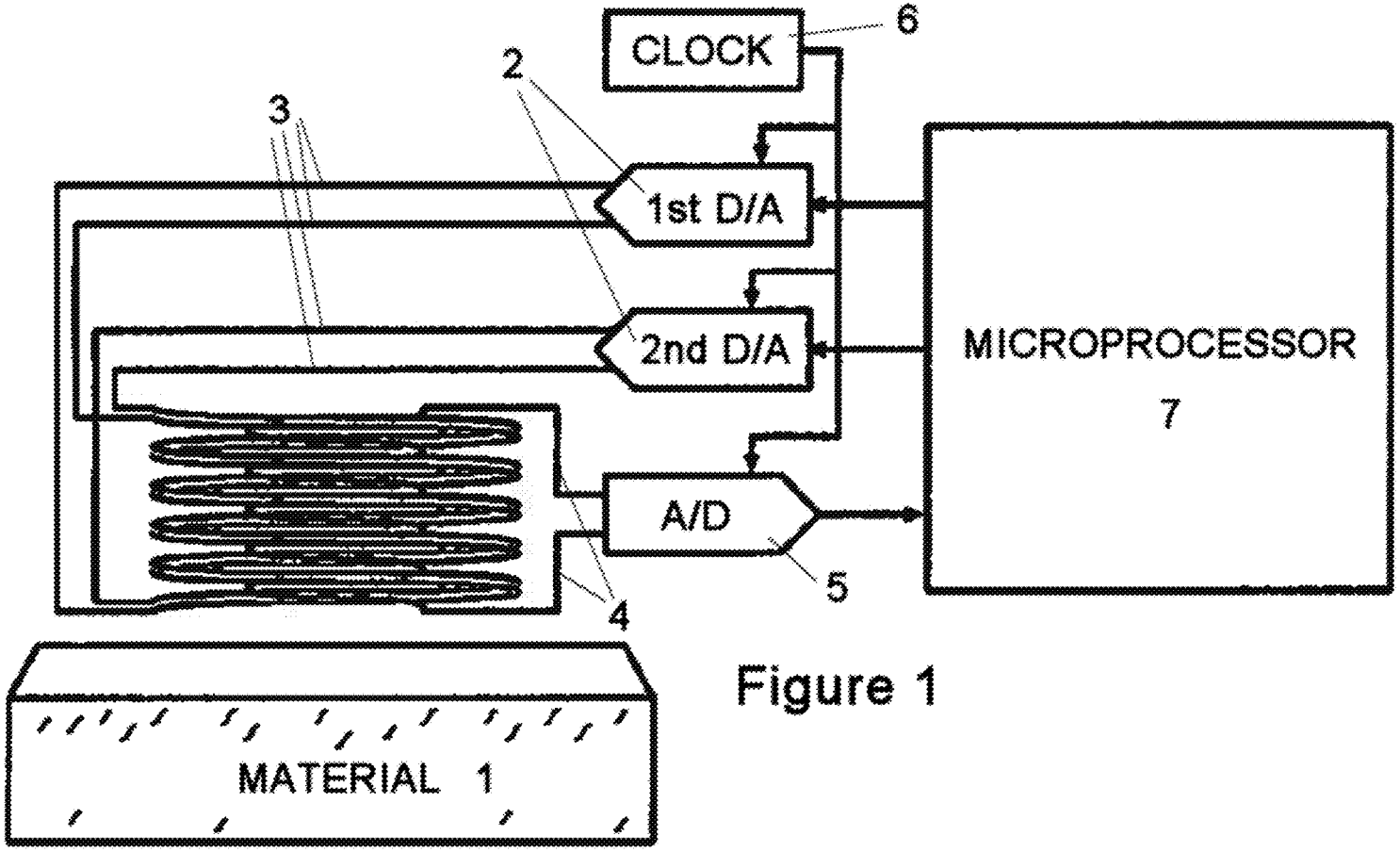
FIG. 1 is a schematic depiction of a probe measurement system of the present invention which may be used in the method of the present invention.

FIG. 1 is a schematic depiction of a probe measurement system of the present invention. The material to be tested 1 is also shown in FIG. 1. Two sinusoidal current generators 2, shown here as D/A 1 and D/A 2, are used to drive a complex varying magnetic field into the sample 1 through two transmitter coils 3. While this example embodiment depicts two transmitter circuits in order to simplify circuit design, a probe could be designed using only one. The transmitter coils 3 preferably have a larger diameter than the thickness of the sample 1 so that the magnetic fields under the center of the transmitter coils 3 are essentially uniform. The transmitter coils 3 are arranged coaxially. A receiver coil 4 is positioned in this region of essentially uniform magnetic fields within the two transmitter coils 3. Voltages induced in the receiver coil 4 are detected and used to determine information related to samples 1 being tested. Preferably an analog-to-digital (A/D) converter 5 is used to convert the induced voltage in the receiver coil 4 into digital samples which are sent to the microprocessor 7. All of the electronics of the probe use a common clock 6.

While the above description of the probe includes two transmitter coils 3 and two sinusoidal current generators 2, this is not the only configuration that will work to achieve the desired measurements. For instance, a single transmitter coil 3 and single generator 2 can be used to produce the two signals. This the least expensive probe to build. The generator 2 is much more expensive since it must have a very low IMD (inter modulation distortion) value. In another configuration, the probe can have a single coil 3 and two generators 2. This embodiment is probably more expensive to build than the single coil/generator embodiment since there are two generators 2, and the final amplifier(s) must able to combine the signals.

In yet another embodiment, the probe may have two coils 3 and a single generator 2. This embodiment is more expensive than the single coil/generator, but the two coils 3 add flexibility. If the two coils 3 are used in "push-pull" mode, the final amplifier would be easier to build. The embodiment described above which includes two coils 3 and two generators 2, is the only high sensitivity configuration that could be built without low IMD components. In a variant on this embodiment, the coils carry apposing DC current components that can cancel or enhance stray magnetic fields.

Finally, there is an embodiment that includes four coils 3 and two generators 2. The coil would be very difficult to build, but the two generators and amplifiers are simpler, since they can both operate in push pull mode. If a second probe is used, the coils in the two probes are connected in series, with the sense of the second signal reversed in the second probe. This cancels out the mutual inductance effect, improving the transmitted signals considerably. This provides the highest possible sensitivity with available technology.

General Use of the Probe

Regardless of the specific configuration of the probe, two sinusoidal signals are created and transmitted into a sample to be tested. The reason for using two signals is now discussed. Voltages are induced in the receiver coil by the transmitted signal(s), and any small changes induced by the sample being tested will be indistinguishable, compared to the power of the transmitted signal. Thus, the power at some other frequency, not present in the transmitted signal, needs to be measured. The test sample will also likely create harmonics of the transmitted signal (i.e. where x is the frequency of transmitted signal, the harmonics would be 2x, 3x, 4x, etc) which will be picked up by the receiver coil. Thus, reading the harmonic signal created by the sample may provide useful information on the sample being tested. Unfortunately, the signal generators will also likely produce harmonics of the transmitted signal, and, again, the signal produced by the sample will likely be small (i.e. noise) compared to the transmitted harmonics. Finally, when two signals are transmitted into the sample, any nonlinear electrical or magnetic properties in the sample being tested will produce intermodulation products of the two transmitted signals, which are also picked up by the receiver coil. Intermodulation product frequencies are additive and subtractive combinations of two or more frequencies. For instance for two frequencies, $F_1$ and $F_2$, some intermodulation product frequencies are $F_1+F_2$; $F_1-F_2$; $2F_1+F_2$; $2F_1-F_2$; $2F_1+2F_2$; etc.

For real world use, the transmitter frequencies, $F_1$ and $F_2$, the A/D converter sampling frequency $F_s$, and the sample size $S_s$ are chosen to meet the following requirements. The sample size $S_s$ is a is an integral power of two (such as, for example, 4096, or 8192, or 16384). $F_s$ is the sampling frequency of the A/D converter in samples/second. Base frequency will be defined as $F_0=F_s/S_s$. $F_1=N\times F_0$; $F_2=P\times F_0$; where N and P are integers with N not equal to P. Also, N and P are chosen such that none of the intermodulation frequencies $F(Q,R)=Q\times F_1+R\times F_2$ are equal to an integral multiple of $F_1$ or $F_2$ for small, non-zero, integer (positive or negative) values of Q and R.

Any nonlinear electrical or magnetic properties in the sample will produce intermodulation products at frequencies F(Q,R). The transmitter apparatus does not produce these frequencies F(Q,R), so the amplitudes of the F(Q,R) components are an absolute measurement of the properties of the nonlinear material. Given that:

$$F(Q,R)=(Q\times N+R\times P)\times F_0=M\times F_0$$

where M is an integer, the amplitudes of the F(Q,R) components are easily obtained using a Fast Fourier Transform or a Finite Impulse Response filter on the set of sample measurements taken by the ND converter.

EXAMPLE OF SPECIFIC USE OF THE PROBE AND TESTING METHOD

The present inventors have found the probe and testing method of the present invention is very useful in determining the state of deterioration of austenitic alloy reformer tubes used in hydrogen reformers. It was noted that deterioration of these austenitic alloys is associated with the appearance of ferromagnetic properties and from this, the inventors determined that it might be possible to predict remaining service life if the amount of deterioration could be measured.

Measurement

The probe and method described is used to measure the health of creep resistant austenitic alloys of the type used in the reformer tubes of hydrogen reformers. It is believed that the probe measures the total magnetic moment and density of certain ferromagnetic micro-zones which can be correlated with the development and deterioration of creep resistance in these alloys. As disclosed above, the method applies two sinusoidal magnetizing fields at slightly different frequencies to the alloy. The magnetic flux resulting from these magnetizing fields as well as the magnetic flux due to induced magnetic moments within the alloy is sampled, processed, and analyzed. Measurements are taken at spaced intervals along the length and circumference of the tubes. This allows for 2d and 3d mapping of the health of the tube.

Analysis

From the total magnetic flux that is received by the receiver coil at each individual testing location, the fundamental and intermodulation frequency signals thereof are isolated. These intermodulation frequency signals provide useful information to analyze the health of the austenitic alloy in the tubes at the specific testing positions. Of particular interest is the third order intermodulation frequencies. The power levels at the intermodulation frequencies are converted into decibels (dB) relative to the fundamental frequency power and plotted in 2D or 3D graphs against the position along the length and/or circumference of the tube. In the same manner as percentages, decibels, in this case $20\times LOG(V_{measured}/V_{reference})$, must always be the ratio of two numbers. Comparison with the fundamental magnitude is most useful because this ratio is independent of receiver characteristics, and not overly sensitive to transmitter characteristics.

Figure 2A:
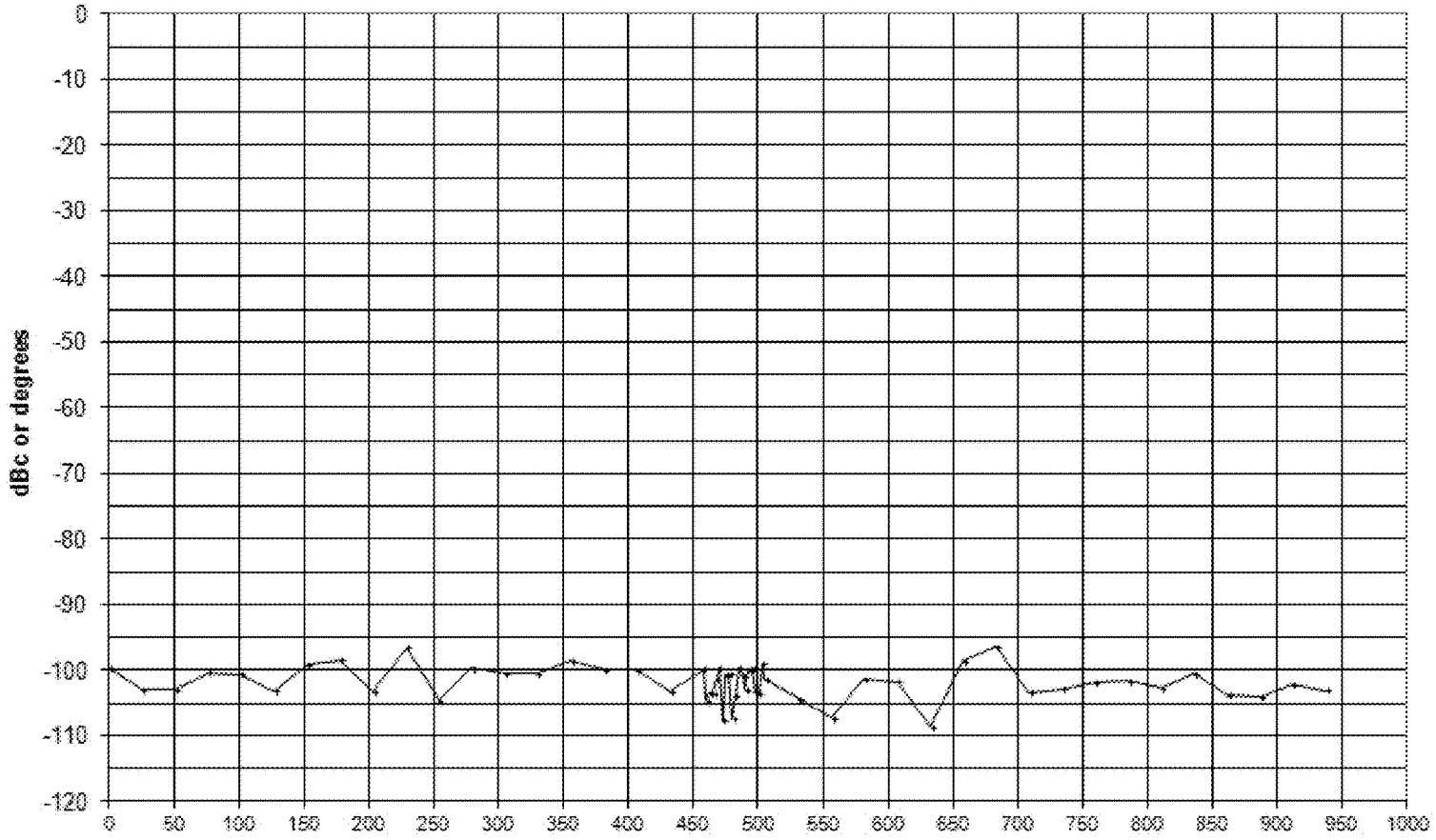
FIGS. 2a and 2b are two dimensional (2D) plots of the intermodulation frequency signals (converted to dB) versus distance along the tube for a brand new reformer tube (2a) and a tube that has been in service for 5 years (2b)
Figure 2B:
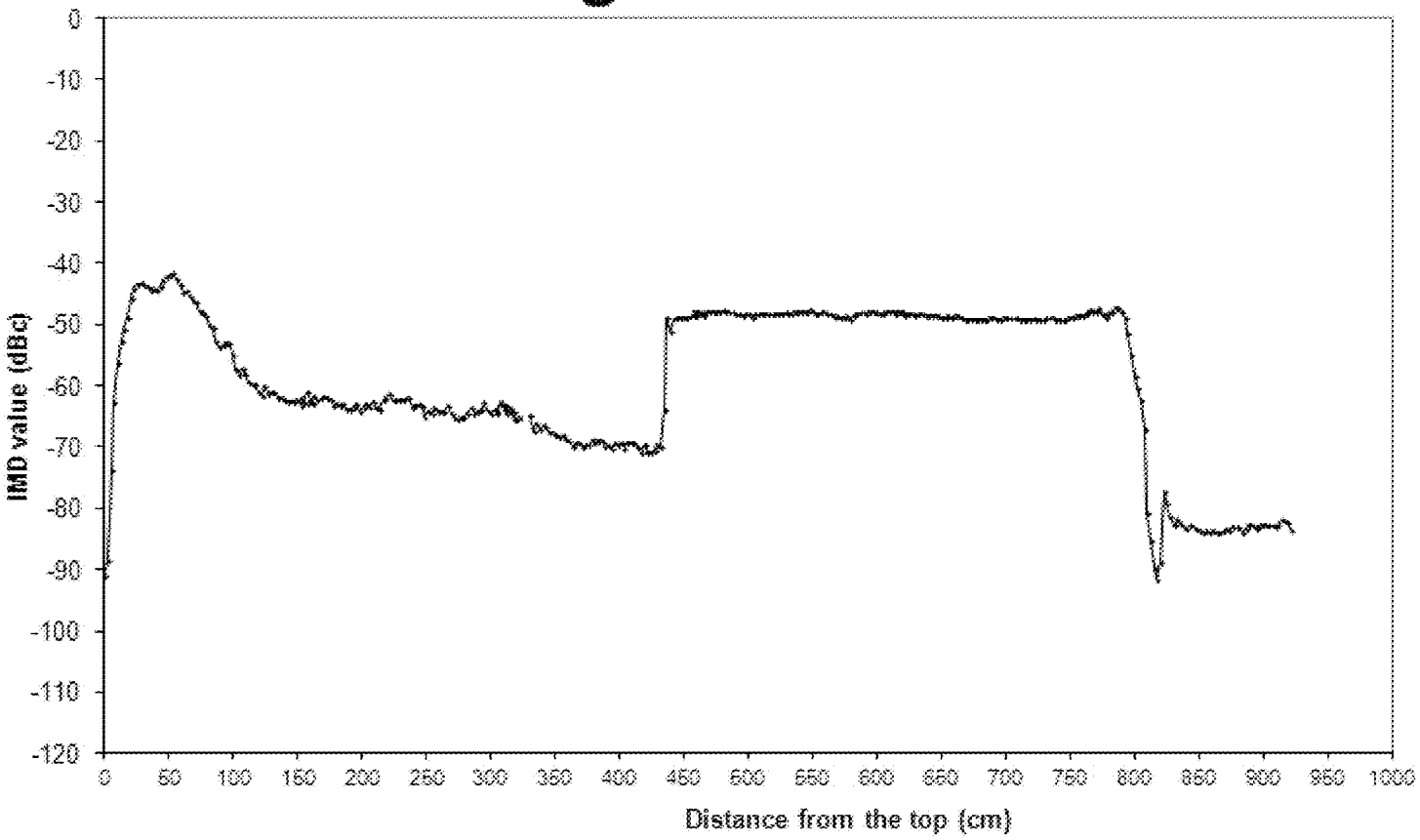

FIGS. 2a and 2b are two dimensional (2D) plots of the intermodulation frequency signals (converted to dB) versus distance along the tube for a brand new reformer tube (with no residual delta ferrite inclusions) and a tube that has been in service for 5 years, respectively). As can be seen from FIG. 2a, the residual free "new" reformer tube has a third order intermodulation frequency response below the noise floor for the existing probes, therefor all that we can see is the uncorrelated electrical noise from the probe itself. Because all that is being recorded is the electrical noise of the probe system, the signal strength (converted to dB) jumps rapidly to any value between −95 dB to −115 dB. Overall, it can be seen that a new tube has a very low intermodulation response signal of, on average, less than 100 dB and this will be taken as the hallmark of an undamaged tube.

In contrast to FIG. 2a, FIG. 2b shows the intermodulation response signal of a tube which, while formed from the very same materials as the tube of FIG. 2a, has been in use in a hydrogen reformer for 5 years. As can be seen, use in the extreme environment of the hydrogen reformer furnace has changed the intermodulation frequency signal response. The signal has increased significantly versus the virgin tube. It should be noted that the very top of the tube is embedded in the furnace ceiling and is attached to a flange. This provides a continuous cooling effect thereby preventing the topmost end from deteriorating as quickly as the tube portions that are exposed to the full thermal effects of the furnace. As can be seen, the response signal of the upper portion of the tube that is exposed to the furnace environment has increased substantially, peaking at about −40 db. This indicates that the tube has significantly deteriorated in that area and may point to a hot spot in the reformer (possibly a hydrogen leak in a neighboring tube). The lower half of the tube is formed of a different alloy than the top half. The reformer tube is actually formed of two tubes which are welded together. The upper tube is formed of a 28Cr/48Ni/Fe type of heat resistant cast alloy while the lower tube is formed of a 25Cr/35Ni/Fe type of heat resistant cast alloy. The lower half has a different reaction to the thermal environment than the top half. The lower half of the tube is relatively uniformly deteriorated and its response signal would indicate that this portion of the tube has at least a reasonable length of life remaining. Finally, similar to the top of the tube, the bottom of the tube is embedded in the floor of the furnace and as such is significantly protected from the thermal effects of the furnace.

Thus the analysis of the intermodulation response signal indicates that the lower half of the 5 year old tube is aging evenly, while the top half is being subjected to a varying furnace environment that may include a "hot spot", which is prematurely aging the uppermost portion of the tube. This premature aging may cause the tube to fail in that area (i.e. cause a hydrogen leak or even break off and fall) which could damage other tubes in its vicinity. Thus, knowledge of the condition of the tube along its entire length allows operators to replace individual tubes as necessary, and also, importantly, allows operators to continue using older tube which have not deteriorated to the point of needing replacement.

Figure 3:
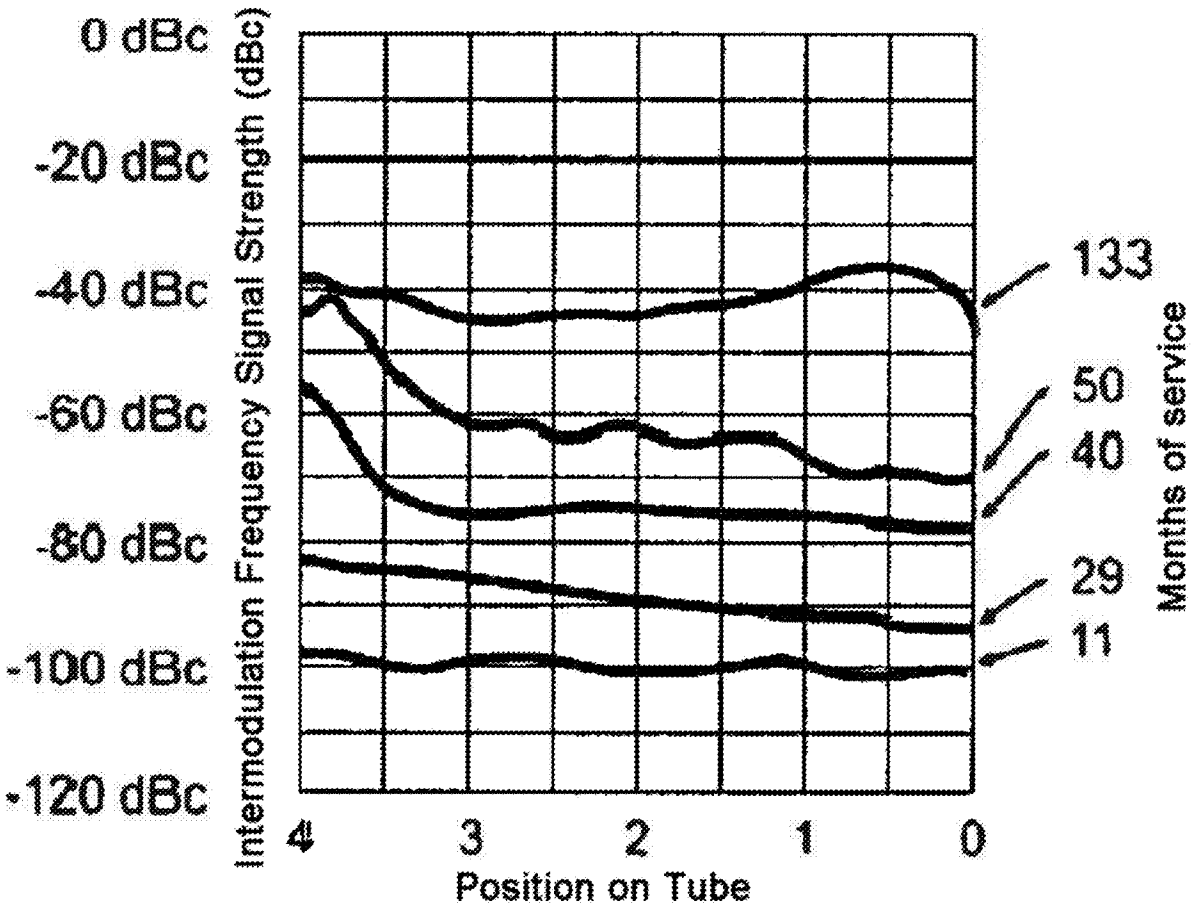
FIG. 3 is a plot of the intermodulation frequency signal converted to dBc along the length of various reformer tubes of the same composition after different length of service within the reformer.

To determine the expected remaining service life of a tube, the measurements of the intermodulation response signal from multiple tubes of different ages were taken (i.e. new tubes, tubes that have been in service in the reformer for varying amounts of time and failed tubes). FIG. 3 is a plot of the intermodulation frequency signal converted to dBc along the length of various reformer tubes of the same composition after different length of service within the reformer. As can be seen, the longer a tube has been in service the stronger the intermodulation frequency signal strength of the tube. Once this data is collected, the remaining service life as a fraction of current age can be determined by comparison with the measurements taken on similar tubes at intervals through their service life.

The remaining service life of the reformer tube as a fraction of the present service life and the actual remaining service life can be estimated by the following formulas:

$$\%\text{ life remaining } L_r=|S_e-S_n|/|S_e-S_0|;\text{ and}$$

$$\text{estimated lifetime remaining } T_r=(L_r/(1-L_r))\times T_n$$

Where $L_r$ is the estimated fraction of life remaining; $S_e$ is the third order intermodulation frequencies signal strength converted into decibels dB of an austenitic steel reformer tube at the end of service life; $S_n$ is the third order intermodulation frequencies signal strength converted into decibels dB of the test sample now; $S_0$ is either the third order intermodulation frequencies signal strength when there is no tube present under the probe, or the third order intermodulation frequencies signal strength of a new tube that has been heated to operating temperature for a few hours, whichever is higher; $T_r$ is the estimated service lifetime remaining for the test sample; and $T_n$ is the present service life of the test sample.

The best value for $S_0$ is the open air calibration point for the probe used to test the tubes, that is, the third order signal strength when there is no tube present. This value generally ranges from −90 to −109 $dB_c$ for the probe and amplifier combinations tested so far. There is reason to believe that the real value for $S_0$ is −120 to −130 $dB_c$, but it is not possible to make meaningful measurements below the open air calibration point of the testing device. The next best value would be taken from a tube that has been brought up to operating temperature for a few hours. This is because new, as cast, tubes can contain an unstable form of delta ferrite sometimes left over from the casting process. This residual disappears upon heating. The impact of this residual on overall tube life is unknown, but it can't be used for the equations presented above. There have been cases where there is no initial IMD for the as cast tube, but this is the exception, not the rule.

As an example let us suppose that the present third order intermodulation frequencies signal strength converted into decibels dB of the tube to be tested is −50 dB, that of a new tube of the same type (alloy composition, processing, etc) as that to be tested is −100 dB, and that of a tube at the end of its service life is −40 db. The fractional remaining service life $L_r$ would be $|-40-(-50)|/|-40-(-100)|=1/6=1/6$. Let us further assume that the present service life of the test sample $T_n$ is 85 months. Then the estimated service lifetime remaining for the test sample $T_r=(1/6/(1-1/6))\times 85$ months=17 months.

It should be noted that the present inventors have learned that the present testing method and equations do not work for tubes with profound damage. In tubes this damaged, the IMD value begins to drop, while the magnitude of the FF or tubes with profound damage, the IMD value begins to drop, while the magnitude of the F2 component at the receiver increases. The effect becomes noticeable at an IMD value of −40 $dB_c$, and by the time F2 reaches half of its maximum value the IMD value reaches −35 dBc. Beyond that point IMD begins to fall as F2 continues to a maximum. In such a case a synthetic IMD value can be projected from this that extends above −35 $dB_c$ and by the time the synthetic IMD value reaches 0 the tube is cracked all the way through.

Deployment/Use of the Probe Via a Crawler

One or more probes may be attached to a transportation device which will allow the probes to traverse the length and width or circumference of the sample to be tested. The transportation device may take the form of a crawler that has the ability to traverse horizontal samples or to climb up and down a vertical sample. Also, depending on the number of probes on the crawler, the crawler may have the ability to turn circumferentially around the sample to reposition the probe to different points on the circumference of the sample. Preferably the crawler includes means for measuring the position of the probe with respect to the dimensions of the sample so that the measured intermodulation frequency signals can be correlated with specific locations on the sample.

The crawler may also carry the supporting electronics for the probe, such as signal generators, A/D and D/A converters, etc. The received intermodulation frequency signals may be recorded onboard the crawler, such as in a dedicated storage medium, for later retrieval. Alternatively, the signals may be transmitted to a separate storage device (wired or wireless transfer). The intermodulation frequency signal processing electronics may be onboard, but preferably are not.

Metallurgical Examination

While not wishing to be bound by theory, the inventors present the following metallurgical explanation behind the measurements/results produced when applying the method and probe of the present invention.

The present method and probe use induced magnetization to detect deterioration in iron nickel chromium carbon alloy tubes. The initial material is not ferromagnetic but loss of chromium and an increase in carbides will change the microstructure and produce ferromagnetic regions with high permeability. It is known that iron nickel chromium alloys get their creep resistance from carbides that precipitate in the as cast matrix, and that additional carbides precipitate and enlarge with time and temperature. It has been discovered that as chromium and iron migrate into these carbides a zone will form near or surrounding the carbides that is enhanced in nickel and depleted in chromium. The resulting ferromagnetic structures are easily driven into saturation by weak magnetizing fields. As creep sets in, chromium is also lost to cracks that form within the alloy, leaving nickel and iron to form thin ferromagnetic sheets within the matrix near the cracks. Once again, these structures are easily driven into saturation by the weak magnetizing field of the probe of the instant invention. These induced magnetic moments contain harmonics and intermodulation products of the original two sinusoidal magnetizing fields that can be related to the size and density of the structures.

Figure 4A:
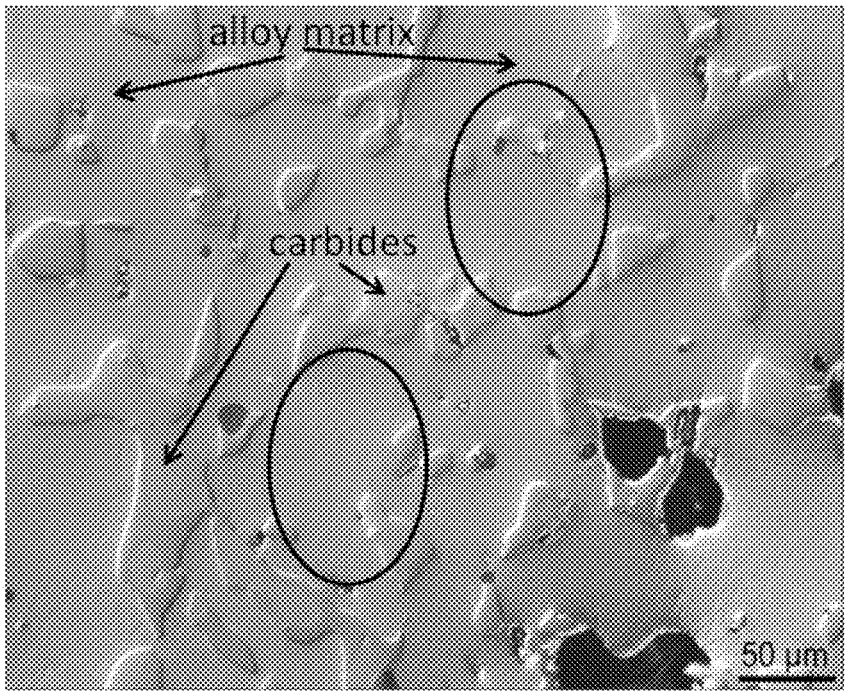
FIGS. 4a and 4b are cross sectional optical micrographs of a used reformer tube sample (type 28% Cr, 48% Ni), which has been in service for 5 years in a cooler section of the reformer.
Figure 4B:
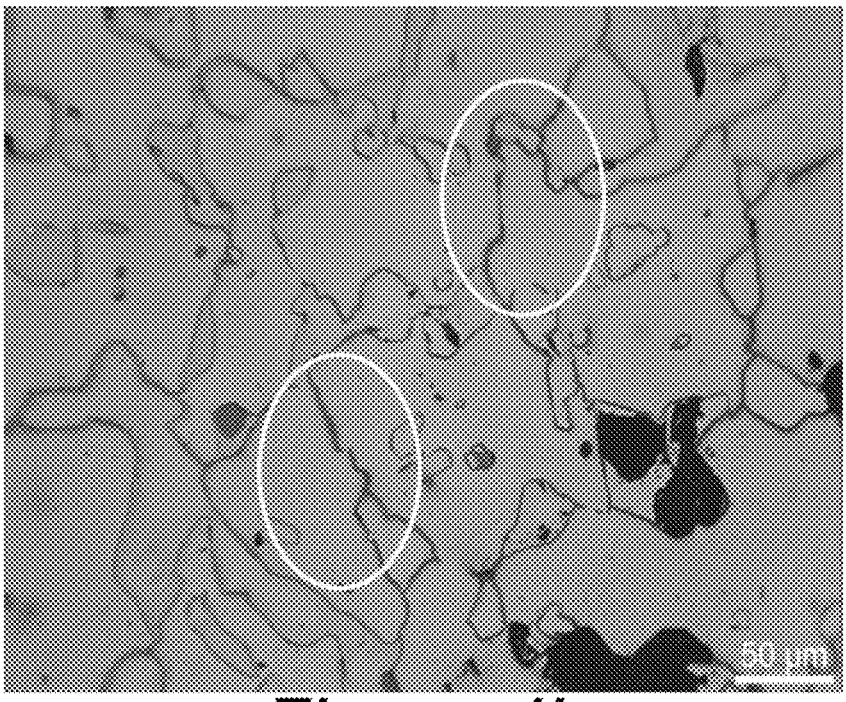

FIGS. 4a and 4b are cross sectional optical micrographs of a used reformer tube alloy sample (type 28% Cr, 48% Ni), which has been in service for 5 years in a cooler section of the reformer. The sample has been taken from the subsurface area of the tube at the inner diameter (ID). The ID surface is at bottom right corner of the photomicrographs. The sample has been metallographically polished, but not etched. In FIG. 4a, the polished surface of the sample is coated with a thin layer of ferrofluid before but no magnetic field has been applied. A ferrofluid is a liquid which becomes strongly magnetized in the presence of a magnetic field. Ferrofluids are colloidal liquids made of nanoscale ferromagnetic, or ferrimagnetic, particles suspended in a carrier fluid (usually an organic solvent or water). Each tiny particle is thoroughly coated with a surfactant to inhibit clumping.

FIG. 4b shows the same sample (as 4a) after a magnetic field has been applied. It can he seen that the ferrofluid migrates to the magnetic areas around the carbides, and to the grain boundaries. Comparing the areas within the ovals between FIGS. 4a and 4b (i.e. before and after applying the magnetic field) it can be seen that there are grain boundaries within the circle that are clearly visible once they attract the ferrofluid.

Figure 5A:
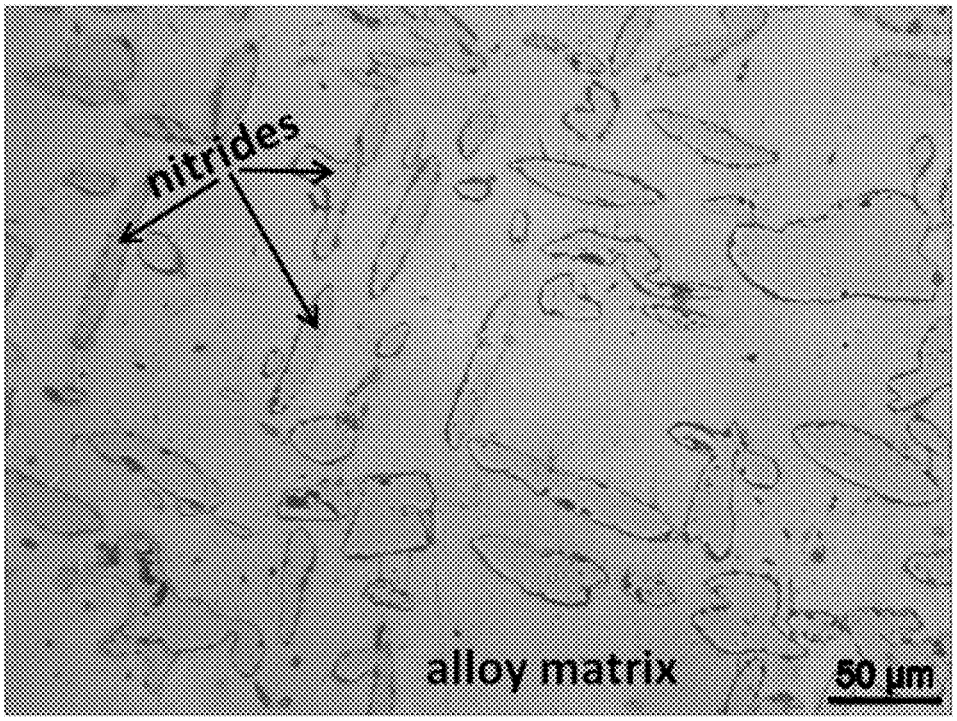
FIGS. 5a and 5b are cross sectional optical micrographs of a used reformer tube sample (type 28% Cr, 48% Ni) which has also been in service for five years, but has been exposed to a hotter region of the furnace.
Figure 5B:
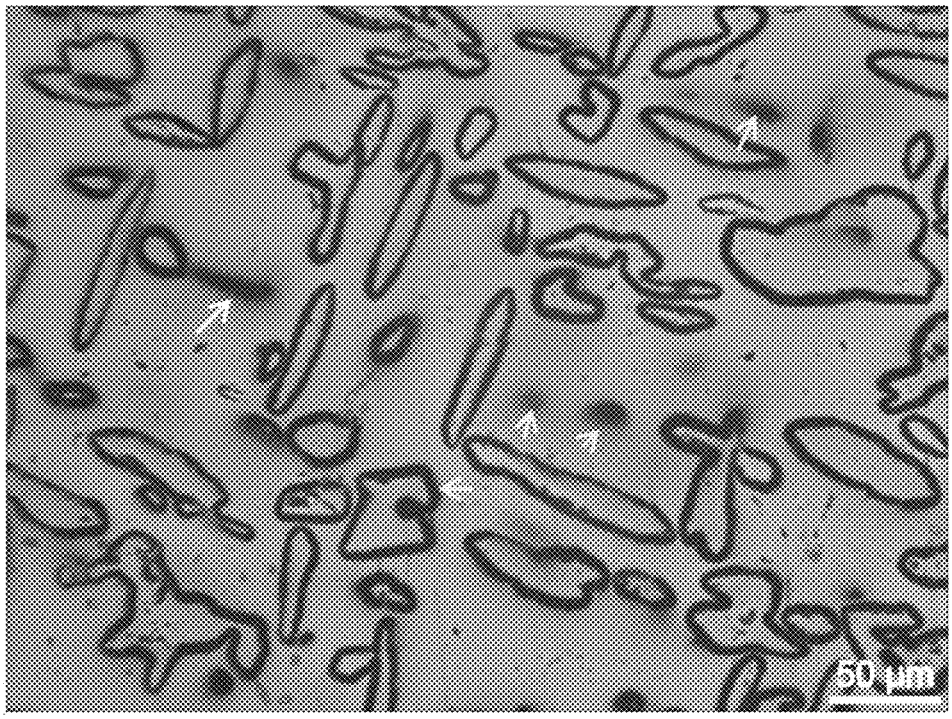

It should be noted that the magnetic regions are confined to narrow regions (below the surface scale) around the carbides, and to the grain boundaries for this sample. However, in a hotter area of the furnace, or as the length of time the tube has been in service increases, the regions (below the surface scale) around the carbides, and the grain boundaries grow. FIGS. 5a and 5b are cross sectional optical micrographs of a used reformer tube sample (type 28% Cr, 48% Ni) which has also been in service for five years, but has been exposed to a hotter region of the furnace. Again, the sample was metallographically polished, but not etched. In FIG. 5a, the polished surface of the sample is coated with a thin layer of ferrofluid as before but no magnetic field has been applied. FIG. 5b shows the same sample (as 5a) after a magnetic field has been applied. It can be seen again that the ferrofluid migrates to the magnetic areas. However, this time it can be seen that the magnetic regions have grown thicker (see the white arrows) and more abundant than those in FIGS. 4a & 4b. This is believed to be because the alloy deteriorates more quickly in the hotter regions, which in turn is believed to be caused by migration of the Cr to the carbide, carbide transformation into Cr-oxides, and ultimately volatilization of some species of Cr-oxides, leaving an ever expanding region which is depleted of Cr. This is why the intermodulation signals increase over the service lifetime of the steel.

Figure 6A:
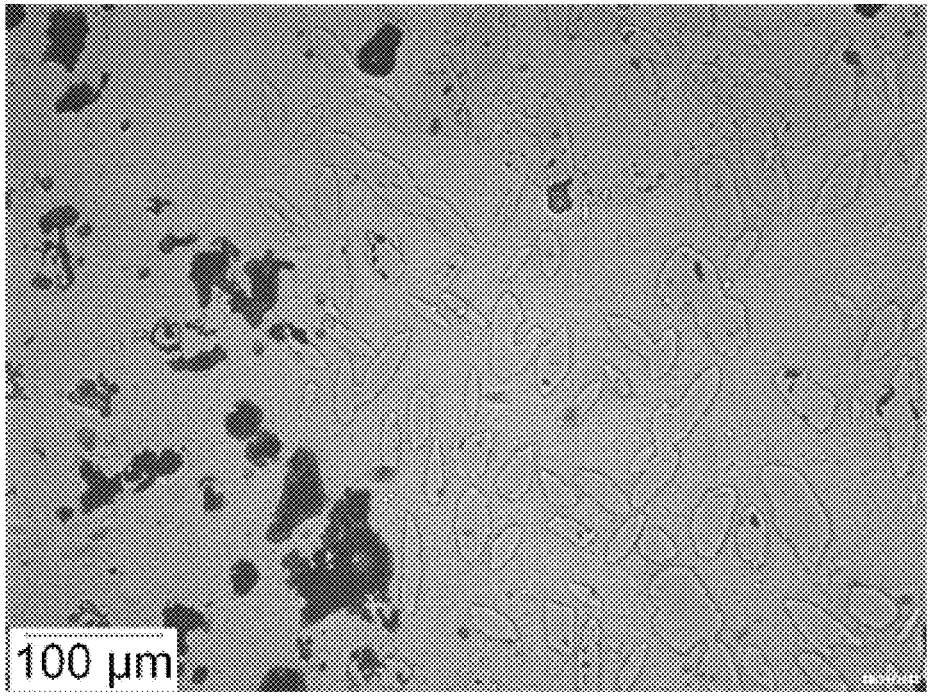
FIGS. 6a and 6b are cross sectional optical micrographs of a used reformer tube sample (type 28% Cr, 48% Ni) which has also been in service for five years, but has been exposed to the hottest region of the furnace.
Figure 6B:
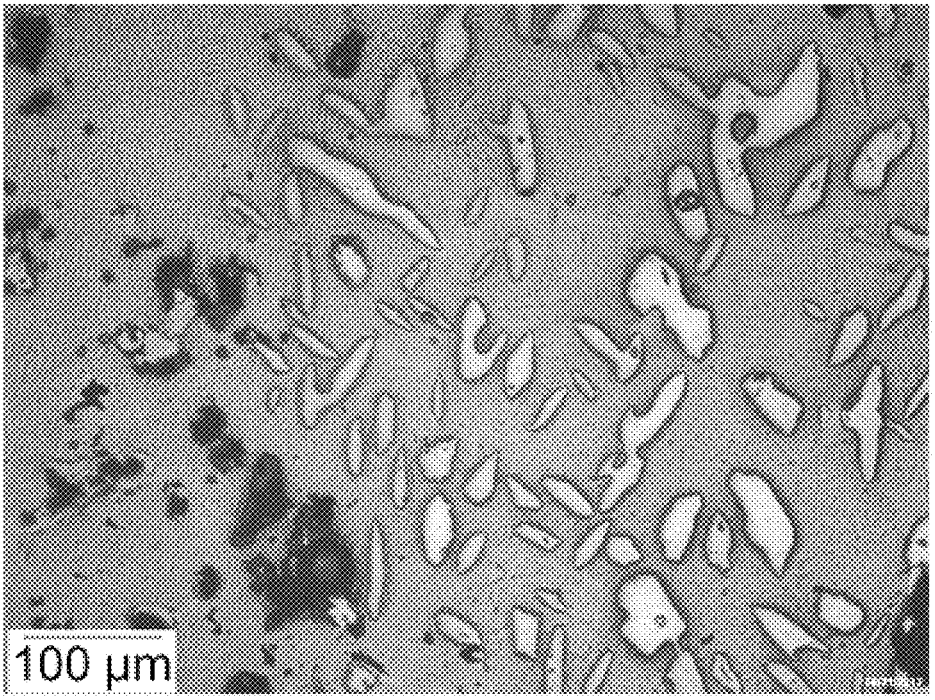

Finally, FIGS. 6a and 6b are cross sectional optical micrographs of a used reformer tube sample (type 28% Cr, 48% Ni) which has also been in service for five years, but has been exposed to the hottest region of the furnace. Again, the sample was metallographically polished, but not etched. In FIG. 6a, the polished surface of the sample is coated with a thin layer of ferrofluid as before but no magnetic field has been applied. FIG. 6b shows the same sample (as 6a) after a magnetic field has been applied. It can now be seen that the ferrofluid migrates out from the carbides and other inclusions and forms a characteristic labyrinthine pattern over the alloy matrix surface. Grain boundaries and sub surface magnetic materials are no longer visible indicating that the entire matrix has become magnetic. At this point intermodulation signals begin to disappear since the magnetizing field is not strong enough to saturate the matrix. At the same time, the magnetic matrix acts like the core of a transformer coupling the transmitter and receiver coils together, thus allowing this region to be detected as an increase in the magnitude of the F2 signal at the receiver.

The foregoing is provided for purposes of explaining and disclosing preferred embodiments of the present invention. Modifications and adaptations to the described embodiments will be apparent to those skilled in the art. These changes and others may be made without departing from the scope or spirit of the invention in the following claims.

We claim:

1. A method of testing an austenitic steel reformer tube comprising:

providing a sample austenitic steel reformer tube to be tested;

choosing one or more testing positions on said an austenitic steel reformer tube;

transmitting two sinusoidal electromagnetic signals, each having a different frequency $F_1$ and $F_2$, into a test position on the austenitic steel reformer tube;

receiving a response signal from said test position; and analyzing said received response signal's fundamental and intermodulation frequencies to determine the state of the austenitic steel reformer tube at said test position;

*wherein said step of receiving a response signal from said test position includes receiving an analog response signal on a receiver coil;*

*wherein said step of receiving a response signal from said test position further includes the step of converting said analog response signal to a digital response signal, using an analog to digital converter;*

*wherein said analog to digital converter has a sampling frequency $F_s$; and*

*wherein said step of converting said analog response signal to a digital response signal, using an analog to digital converter includes combining a multiple of samples into a single representative sample, the number of samples which are combined into said single representative sample being designated the sample size $S_s$.*

[2. The method of claim 1, wherein said step of receiving a response signal from said test position includes receiving an analog response signal on a receiver coil.]

[3. The method of claim 2, wherein said step of receiving a response signal from said test position further includes the step of converting said analog response signal to a digital response signal, using an analog to digital converter.]

[4. The method of claim 3, wherein said analog to digital converter has a sampling frequency $F_s$.]

[5. The method of claim 4, wherein said step of converting said analog response signal to a digital response signal, using an analog to digital converter includes combining a multiple of samples into a single representative sample, the number of samples which are combined into said single representative sample being designated the sample size $S_s$.]

6. The method of claim [5] *1*, wherein said sample size $S_s$ [is a] is an integral power of 2.

7. The method of claim 6, wherein said sample size $S_s$ is a number selected from the group consisting of 4096, 8192, and 16384 samples.

8. The method of claim 7, wherein said sampling frequency $F_s$ is 44100 samples per second.

9. The method of claim 5, wherein said step of transmitting two sinusoidal electromagnetic signals includes the step of defining a base frequency $F_0$, wherein $F_0=F_s/S_s$.

10. The method of claim 9, wherein said step of transmitting two sinusoidal electromagnetic signals further includes the step of choosing said two frequencies F1 and F2 such that:

$$F_1=N\times F_0;$$

$$F_2=P\times F_0;$$

where N and P are integers with N not equal to P, and

N and P are chosen such that none of the intermodulation frequencies, $F(Q,R)=Q\times F_1+R\times F_2$ are equal to an integral multiple of $F_1$ or $F_2$ for small, non-zero, integer (positive or negative) values of Q and R.

11. The method of claim 1, wherein said step of transmitting two sinusoidal electromagnetic signals comprises transmitting both of said signals from a single transmitter coil.

12. The method of claim 1, wherein said step of transmitting two sinusoidal electromagnetic signals comprises transmitting each of said signals from individual transmitter coils.

13. [The method of claim 12,] *A method of testing an austenitic steel reformer tube comprising:*

*providing a sample austenitic steel reformer tube to be tested;*

*choosing one or more testing positions on said an austenitic steel reformer tube;*

*transmitting two sinusoidal electromagnetic signals, each having a different frequency $F_1$ and $F_2$, into a test position on the austenitic steel reformer tube;*

*receiving a response signal from said test position; and*

*analyzing said received response signal's fundamental and intermodulation frequencies to determine the state of the austenitic steel reformer tube at said test position;*

*wherein said step of transmitting two sinusoidal electromagnetic signals comprises transmitting each of said signals from individual transmitter coils; and* wherein said transmitter coils have a larger diameter than the thickness of the sample tube to be tested.

14. The method of claim 1, wherein said step of transmitting two sinusoidal electromagnetic signals comprises creating analog sinusoidal electromagnetic signals using at least one digital-to-analog signal generator.

15. The method of claim 14, wherein said two sinusoidal electromagnetic signals are created by two signal generators.

16. The method of claim 1, wherein said step of analyzing said received response signal's fundamental and intermodulation frequencies comprises analyzing the first order fundamental and the third order intermodulation frequencies of said received response signal.

17. The method of claim 16, wherein said fundamental is $F_2$ and said third order intermodulation frequencies are $2F_1+F_2$ and $F_1+2F_2$.

18. The method of claim 16, wherein said step of analyzing the third order intermodulation frequencies comprises converting the amplitude of said third order intermodulation frequencies into decibels dB relative to the amplitude of said fundamental.

19. The method of claim 18, wherein the strength of said third order intermodulation frequencies which have been converted into decibels dB is compared to the same measurement of brand new and end of service life austenitic steel reformer tubes, said comparison providing a qualitative measure of the health of said austenitic steel reformer tube.

20. [The method of claim 19,] *A method of testing an austenitic steel reformer tube comprising:*

*providing a sample austenitic steel reformer tube to be tested;*

*choosing one or more testing positions on said an austenitic steel reformer tube;*

*transmitting two sinusoidal electromagnetic signals, each having a different frequency $F_1$ and $F_2$, into a test position on the austenitic steel reformer tube;*

*receiving a response signal from said test position; and*

*analyzing said received response signal's fundamental and intermodulation frequencies to determine the state of the austenitic steel reformer tube at said test position;*

*wherein said step of analyzing said received response signal's fundamental and intermodulation frequencies comprises analyzing the first order fundamental and the third order intermodulation frequencies of said received response signal;*

*wherein said step of analyzing the third order intermodulation frequencies comprises converting the amplitude of said third order intermodulation frequencies into decibels dB relative to the amplitude of said fundamental;*

*wherein the strength of said third order intermodulation frequencies which have been converted into decibels dB is compared to the same measurement of brand new and end of service life austenitic steel reformer tubes, said comparison providing a qualitative measure of the health of said austenitic steel reformer tube; and* including the further step of estimating the remaining service life of said austenitic steel reformer tube as a fraction of the present service life of said austenitic steel reformer tube by the following formulas:

$$\text{fractional life remaining } L_r=|S_e-S_n|/|S_e-S_0|; \text{ and}$$

$$\text{estimated lifetime remaining } T_r=(L_r/(1-L_r))\times T_n$$

where:

$L_r$ is the estimated percentage of life remaining;

$S_e$ is the third order intermodulation frequencies signal strength converted into decibels dB of an austenitic steel reformer tube at the end of service life;

$S_n$ is the third order intermodulation frequencies signal strength converted into decibels dB of the test sample now;

$S_0$ is either the third order intermodulation frequencies signal strength when there is no tube present under the probe, or the third order intermodulation frequencies signal strength of a new tube that has been heated to operating temperature for a few hours, whichever is higher;

$T_r$ is the estimated service lifetime remaining for the test sample; and $T_n$ is the present service life of the test sample.

* * * * *